United States Patent [19]

Morita et al.

[11] Patent Number: 5,087,640
[45] Date of Patent: Feb. 11, 1992

[54] NOVEL CYANOGUANIDINE DERIVATIVES

[75] Inventors: Tominori Morita, Nishinomiya; Kazuya Yoshiizumi; Noriyasu Nishimura, both of Osaka; Katsumi Goto, Kagoshima; Takayuki Sukamoto, Osaka; Kohichiro Yoshino, Suita, all of Japan

[73] Assignee: Kanebo, Ltd., Tokyo, Japan

[21] Appl. No.: 544,448

[22] Filed: Jun. 27, 1990

[30] Foreign Application Priority Data

Jun. 28, 1989 [JP] Japan .................................. 1-166119

[51] Int. Cl.$^5$ ............................................ A61K 31/155
[52] U.S. Cl. ...................................... 514/609; 504/104
[58] Field of Search ........................ 564/104; 514/609

[56] References Cited

U.S. PATENT DOCUMENTS

| | | | |
|---|---|---|---|
| 4,639,268 | 1/1987 | Arotin et al. | 564/104 |
| 4,804,780 | 2/1989 | Speltz et al. | 564/104 |
| 5,011,837 | 4/1991 | Atwal et al. | 564/104 |

FOREIGN PATENT DOCUMENTS 0037971 10/1981 European Pat. Off. ............ 564/104

*Primary Examiner*—James H. Reamer
*Attorney, Agent, or Firm*—Millen, White & Zelano

[57] ABSTRACT

Compounds of the formula:

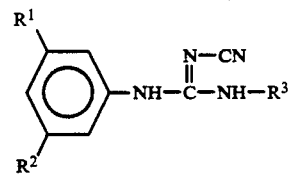

wherein $R^1$ and $R^2$ are independently fluorine, chlorine or bromine atom, and $R^3$ is a $C_4$-$C_7$ alkyl having at least a branch at the $C_1$ position, exhibit $K^+$ channel opening activity and are useful as hypotensive agents and coronary vasodilators.

15 Claims, No Drawings ns
NOVEL CYANOGUANIDINE DERIVATIVES

BACKGROUND OF THE INVENTION

This invention relates to novel cyanoguanidine derivatives useful as therapeutic agents for circulation system disorders such as hypertension, angina pectoris and the like.

It is known that there are several ion channels in the cell membranes of smooth muscle such as vascular smooth muscle. These channels include sodium ion ($Na^+$) channels, potassium ion ($K^+$) channels, calcium ion ($Ca^{++}$) channels etc. which selectively regulate the permeability to their respective ions in the cell. These channels function to regulate the contraction and relaxation of the smooth muscle by opening or closing the channels in response to the modulation of receptors or potentials on the cell membranes. When $K^+$ channels are opened, the increased permeability of the cell membrane allows more potassium ions to migrate outwardly so that the membrane potential shifts toward more negative values. Once this has occured, the opening of voltage-dependent $Ca^{++}$ channels would be counteracted to reduce the influx of $Ca^{++}$ ions into the cell because the $Ca^{++}$ channels are activated only at a membrane potential above a threshold value. Consequently, drugs having $K^+$ channel opening activity known as $K^+$ channel openers can relax vascular smooth muscle and are useful as hypotensive and coronary vasodilating agents.

Pinacidil, chemically N-cyano-N'-(4-pyridyl)-N''-(1,2,2-trimethylpropyl)guanidine monohydrate, is one of known $K^+$ channel openers. See, U.S. Pat. No. 4,057,636 and I. Ahnfelt-Ronne, J. Cardiovascular Pharmacol., 12, (Suppl. 2): S1–S4 (1988). A number of homologs and analogs of pinacidil were also investigated. See, H. J. Petersen et al., J. Med. Chem., 21, 773 (1978). U.S. Pat. No. 4,567,188 to Niemers et al. discloses a class of 1,1-ethenediamine compounds useful as hypotensive agents.

SUMMARY OF THE INVENTION

It is a principal object of the present invention to provide a class of novel compounds having more potent $K^+$ channel opening activity than the known compounds. Other objects and advantages of the invention will become apparent to those skilled in the art as the description preceeds.

Surprisingly, it has been discovered that certain N-cyano-N'-(3,5-dihalopheny)-N''-branched chain alkylguanidines open $K^+$ channels in the cell membrane of smooth muscle in a manner more potent than pinacidil and other known compounds.

Therefore, the present invention provides a compound of the formula (I):

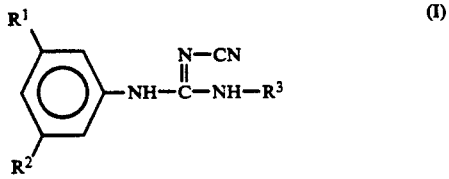

wherein $R^1$ and $R^2$ independently represent fluorine, chlorine or bromine atom, and $R^3$ represents a $C_4$-$C_7$ alkyl group having at least one branch on the $C_1$ position.

In another aspect, the present invention provides a method for preparing the novel compound of the formula (I) above which comprises reacting a compound of the formula (III):

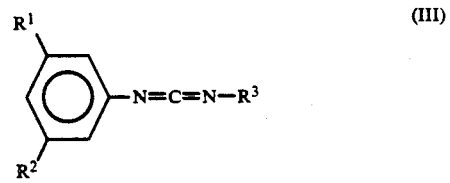

wherein $R^1$, $R^2$ and $R^3$ are as defined, with cyanamide.

DETAILED DISCUSSION

In the formula (I), $R^1$ and $R^2$ may independently represent F, Cl or Br atom. $R^3$ may represent a $C_4$-$C_7$ alkyl having at least one branch at the $C_1$ position. Examples of such alkyls include t-butyl, t-penty, 1,1-dimethylbutyl, 1-ethyl-1-methylpropyl, 1,1-diethylpropyl, 1,2,2-trimethylpropyl, 1,1,2-trimethylpropyl and the like.

Tautomers may be present with regard to the compounds of the formula (I). It is, therefore, intended by the present invention to cover such tautomers as well.

As examples of specific compounds of particular interest, the following compound may be mentioned:
N-cyano-N'-(3,5-dichlorophenyl)-N''-t-pentylguanidine;
N-cyano-N'-(3,5-dichlorophenyl)-N''-(1,1-dimethylbutyl)guanidine;
N-cyano-N'-(3,5-dichlorophenyl)-N''-(1-ethyl-1-methylpropyl)guanidine; and
N-(3-bromo-5-fluorophenyl)-N'-cyano-N''-t-pentylguanidine.

The compounds of the formula (I) may be prepared by reacting a corresponding carbodiimide of the formula (III):

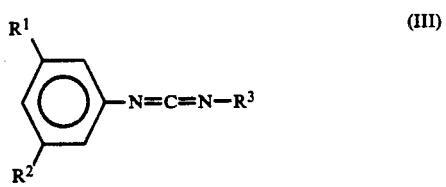

wherein $R^1$, $R^2$ and $R^3$ are as defined, with cyanamide. The reaction may be performed in an inert solvent such as tetrahydrofuran (THF), N,N-dimethylformamide (DMF) and dimethylsulfoxide (DMSO) by heating the reactants at a temperature from 50° C. to the boiling point of the solvent used. The reaction time varies with the temperature and may be generally from 30 minutes to 72 hours. Usually cyanamide is used in excess up to 10 times on equivalent basis relative to the starting carbodiimide. A suitable base such as diisopropylethylamine may be used in this reaction as a catalyst.

After the reaction, the compounds of the formula (I) may be isolated and purified by any conventional method such as column chromatography and/or recystallization.

The starting compounds of the formula (III) are also novel compounds. They may be synthesized by either one of the following method A or method B.

Method A comprises reacting a thiourea derivative of the formula (II):

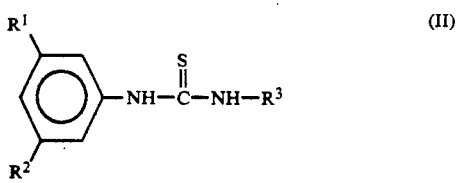

wherein $R^1$, $R^2$ and $R^3$ are as defined, with triphenylphosphine and carbon tetrachloride in the presence of a base such as triethylamine in an inert organic solvent. The reaction may be performed by heating the reaction mixture at a temperature from room temperature to the boiling point of the solvent used for 2 to 6 hours. Examples of suitable solvents include dichloromethane and the like. Triphenylphosphine, carbon tetrachloride and the base may be used in excess up to 4 times on equivalent basis relative to the thiourea derivative.

Method B comprises reacting the thiourea derivative of the formula (II) with dicyclohexylcarbodiimide (DCC) in an inert organic solvent in the presence of a base such as triethylamine. The reaction may be performed by heating the reaction mixture at a temperature from room temperature to the boiling point of the solvent used for 2 to 12 hours. Examples of suitable solvents include THF, acetonitrile and like. DCC may be used in 1 to 2 times on equivalent basis relative to the thiourea derivative. The base may be used in 0.1 to 0.5 equivalent relative to the thiourea derivative. Method B may be combined with the reaction of the compound of the formula (III) with cyanamide by additionally incorporating cyanamide into the reaction mixture to produce the compound of the formula (I) without isolating the intermediate carbodiimide derivative of the formula (III).

The thiourea derivatives of the formula (II) are also novel compounds. They may be produced by reacting 3,5-dihaloaniline of the formula (IV):

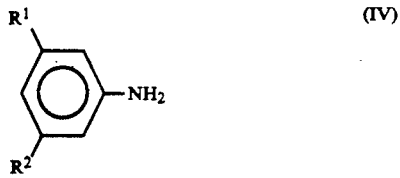

wherein $R^1$ and $R^2$ are as defined, with thiophosgene in an inert organic solvent at a temperature from room temperature to the boiling temperature of the solvent used for a period from 30 minutes to 6 hours, and then reacting the resultant isothiocyanate compound of the formula (V):

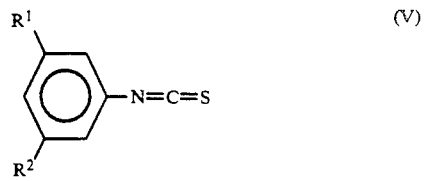

wherein $R^1$ and $R^2$ are as defined, with an alkylamine of the formula (VI):

$$R^3-NH_2 \qquad (VI)$$

wherein $R^3$ is as defined, in an inert organic solvent at a temperature from 0° C. to room temperature for a period of 15 minutes to 3 hours. Examples of usable solvents include benzene, ethyl acetate and the like.

The compounds of the present invention exhibit a potent $K^+$ channel opening activity and a relatively low toxicity.

The compounds of the present invention may be administered to human subjects orally or intraveneously or in any other suitable mode of administration. Oral administration in the form of tablets, granules, powders, capsules and the like containing an amount of the active compound effective for the treatment of circulation system disorders including hypertention and angina pectoris is preferable. These formulations may contain conventional excipients or carriers such as lactose, synthetic alminum silicate, glucose and mannitol; disintegrants such as CMC, and sodium arginate; lubricants such as magnesium stearate and talc; and/or binders such as corn starch and PVP. The suitable dose range may vary with the severity of disease, mode of administration and the nature of specific active compounds, and may be easily determined by those skilled in the art.

The following examples are offered for illustrating purposes only. All percents therein are by weight unless otherwise indicated.

PART A. PREPARATION OF STARTING MATERIALS

EXAMPLE A-1

N-t-butyl-N'-(3,5-dichlorophenyl)thiourea

To a solution of 32.3 g of 3,5-dichloroaniline in 200 ml of benzene was added 7.6 g of thiophosgene in 10 ml of benzene dropwise under reflux. The mixture was stirred at the same temperature for 1.5 hours, cooled to room temperature and filtered to remove insoluble matter. The filtrate was evaporated in vacuo and the resulting solid was dissolved in 150 ml of ethyl acetate. To the solution was added 6.0 g of t-butylamine dropwise under ice-cooling while stirring. The mixture was stirred at room temperature for 2 hours and then evaporated in vacuo. The resulting solid was filtered off and recrystallized from benzene to give 14.8 g of the title compound as colorless needles melting at 164.0°–165.0° C.

NMR (DMSO-$d_6$, $\delta$ ppm): 1.48 (9H, s), 7.22 (1H, t), 7.61 (2H, d), 7.75 (1H, bs), 9.52 (1H, bs).

Analysis calculated for $C_{11}H_{14}Cl_2N_2S$: C 47.66; H 5.09; N 10.11; Found: C 47.67, H 5.07; N 10.13.

EXAMPLE A-2

N-(3,5-dichlorophenyl)-N'-t-pentylthiourea

To a solution of 7.8 g of 3,5-dichloroaniline in 100 ml of benzene was added 1.8 g of thiophosgene in 5 ml of benzene dropwise under reflux. The mixture was stirred at the same temperature for 1.5 hours, cooled to room temperature and filtered to remove insoluble matter. The filtrate was evaporated in vacuo and the resulting solid was dissolved in 50 ml of ethyl acetate. To the solution was added 1.7 g of t-pentylamine dropwise under ice-cooling while stirring. The mixture was stirred at room temperature for 2 hours and then evaporated in vacuo. The resulting solid was filtered off and recrystallized from cyclohexane-ethyl acetate mixture to give 3.5 g of the title compound as colorless needles melting at 134.0°–136.0° C.

NMR (DMSO-$d_6$, δ ppm): 0.82 (3H, t), 1.42 (6H, s), 1.93 (2H, q), 7.23 (1H, t), 7.5–7.7 (3H, m) 9.55 (1H, bs).

Analysis calculated for $C_{12}H_{16}Cl_2N_2S$: C 49.49; H 5.54; N 9.62; Found: C 49.58; H 5.47; N 9.59.

EXAMPLE A-3

N-(3,5-dichlorophenyl)-N'-(1,1-dimethylbutyl)thiourea

To a solution of 6.0 g of 3.5-dichloroaniline in 50 ml of benzene was added 1.4 g of thiophosgene. The mixture was stirred at room temperature for 1 hour and filtered to remove insoluble matter. After the addition of 3.0 g of 1,1-dimethylbutylamine, the mixture was stirred at the same temperature for 1 hour and then evaporated in vacuo. The resulting crystals were recovered by filtration and washed with small amount of cyclohexane to give 3.0 g of the title compound. Recrystallization of a portion thereof from benzene-n-hexane mixture gave a sample for analysis melting at 115.0°–117.0° C.

NMR (CDCl$_3$, δ ppm): 0.94 (3H, t), 1.2–1.4 (2H, m), 1.49 (6H, s), 1.8–1.9 (2H, m), 6.03 (1H, bs), 7.0–7.2 (2H, m), 7.23 (1H, t), 7.61 (1H, bs).

Analysis calculated for $C_{13}H_{18}Cl_2N_2S$: C 51.15; H 5.94; N 9.14; Found: C 51.14; H 5.83; N 9.22.

EXAMPLE A-4

N-(3,5-dichlorophenyl)-N'-(1,1,2-trimethylpropyl)thiourea

A solution of 5.0 g of 3,5-dichloroaniline and 1.2 g of thiophosgene in 100 ml of benzene was refluxed for 3 hours. The mixture was cooled to room temperature and filtered to remove insoluble matter. To the filtrate was added 3.0 g of 1,1,2-trimethylpropylamine. The mixture was stirred at the same temperature for 1 hour and evaporate in vacuo. A small amount of cyclohexane was added to the residue. The resulting crystals were recovered by filtration to give 2.5 g of the title compound. Recrystallization of a portion thereof from cyclohexane gave an analytical sample melting at 132.0°–134.0° C.

NMR (CDCl$_3$, δ ppm): 0.91 (6H, d), 1.47 (6H, s), 2.5–2.7 (1H, m), 6.03 (1H, bs), 7.1–7.2 (2H, m), 7.24 (1H, t), 7.35 (1H, bs).

Analysis calculated for $C_{13}H_{18}Cl_2N_2S$: C 51.15; H 5.94; N 9.18; Found: C 51.20; H 5.74; N 9.16.

EXAMPLE A-5

N-(3,5-dichlorophenyl)-N'-(1-ethyl-1-methylpropyl)thiourea

To a solution of 11.1 g of 3,5-dichloroaniline in 140 ml of benzene was added 2.6 g of thiophosgene in 10 ml of benzene dropwise under reflux. The mixture was stirred at the same temperature for 1.5 hours, cooled to room temperature and filtered to remove insoluble matter. To the filtrate was added 2.3 g of 1-ethyl-1-methylpropylamine in 50 ml benzene dropwise and the mixture stirred at room temperature for 2 hours. The reaction mixture was evaporated. The resulting solid was recovered by filtration and recrystallized from cyclohexane to give 4.9 g of the title compound as colorless needles melting at 128.5°–131.5° C.

NMR (CDCl$_3$, δ ppm): 0.88 (6H, t), 1.40 (3H, s), 1.7–2.1 (4H, m), 5.88 (1H, bs), 7.15 (2H, s), 7.23 (1H, t), 7.56 (1H, bs).

Analysis calculated for $C_{13}H_{18}Cl_2N_2S$: C 51.15; H 5.94; N 9.18; Found: C 51.17; H 5.89; N 9.17.

EXAMPLE A-6

N-(3,5-dichlorophenyl)-N'-(1,2,2-(trimethylpropyl)thiourea

To a solution of 8.0 g of 3,5-dichloroaniline in 100 ml of benzene was added 1.9 g of thiophosgene in 5 ml of benzene dropwise under reflux. The mixture was stirred at the same temperature for 1.5 hours, cooled to room temperature and filtered to remove insoluble matter. The filtrate was evaporated in vacuo and the resulting solid was dissolved in 50 ml of ethyl acetate. To the solution was added 1.7 g of 1,2,2-trimethylpropylamine dropwise under icecooling. The solution was stirred at room temperature for 2 hours and evaporated in vacuo. The resulting solid was filtered off and recrystallized from cyclohexane-ethyl acetate mixture to give 3.1 g of the title compound as colorless needles melting at 152.0°–154.0° C.

NMR (DMSO-$d_6$, δ ppm): 0.92 (9H, s), 1.05 (3H, d), 4.2–4.4 (1H, m), 7.23 (1H, t), 7.73 (2H, d), 7.89 (1H, d), 9.86 (1H, bs).

Analysis calculated for $C_{13}H_{18}Cl_2N_2S$: C 51.15; H 5.94; N 9.18; Found: C 51.26; H 5.97; N 9.18.

EXAMPLE A-7

N-(3,5-dichlorophenyl)-N'-(1,1-diethylpropyl)thiourea

To a solution of 970 mg of 3,5-dichloroaniline in 4 ml of benzene was added 230 mg of thiophosgene in 1 ml of benzene dropwise under reflux. The mixture was stirred at the same temperature for 1.5 hours, cooled to room temperature and filtered to remove insoluble matter. To the filtrate was added 230 mg of 1,1-diethylpropylamine dropwise. The mixture was stirred at room temperature for 2 hours and evaporated in vacuo. The resulting solid was chromatographed on a silica gel column using as a solvent a 50:1 mixture of cyclohexane and ethyl acetate, and then recrystallized from cyclohexane to give 120 mg of the title compound as colorless needles melting at 151.5°–153.5° C.

NMR (CDCl$_3$, δ ppm): 0.84 (9H, t), 1.87 (6H, q), 5.71 (1H, bs), 7.0–7.3 (3H, m), 7.57 (1H, bs).

Analysis calculated for $C_{14}H_{20}Cl_2N_2S$: C 52.66; H 6.31; N 8.77; Found: C 52.64; H 6.33; N 8.74.

EXAMPLE A-8

N-t-butyl-N'-(3,5-difluorophenyl)thiourea

A solution of 5.0 g of 3,5-difluoroaniline and 1.4 g of thiophosgene in 50 ml of benzene was refluxed for 2 hours, cooled to room temperature and filtered to remove insoluble matter. The filtrate was evaporated in vacuo. The residue was taken in 40 ml of DMF and reacted with 7.0 g of t-butylamine at room temperature for 20 minutes with stirring. The reaction mixture was poured into 600 ml of water. The resulting crystals were recovered by filtration to give 2.5 g of the title compound. Recrystallization of a portion thereof from cyclohexane gave an analytical sample melting at 140.0°–142.0° C.

NMR (CDCl$_3$, δ ppm): 1.55 (9H, s), 6.17 (1H, bs), 6.6–6.8 (3H, m), 7.51 (1H, bs).

Analysis calculated for $C_{11}H_{14}F_2N_2S$: C 54.08; H 5.78; N 11.47; Found: C 54.04; H 5.72; N 11.48.

EXAMPLE A-9

N-t-butyl-N'-(3,5-dibromophenyl)thiourea 11.0 g of 3,5-dibromoaniline produced by the method described in Kogyo Kagaku Zasshi, 59(6), 133(1956) was dissolved in 150 ml of benzene. After the addition of 1.7 g of thiophosgene, the solution was refluxed for 3 hours, cooled to room temperature and filtered to remove insoluble matter. To the filtrate was added 5.3 g of t-butylamine and the mixture stirred at room temperature for 1 hour. The resulting crystals were filtered off to give 3.6 g of the title compound.

Recrystallization of a portion thereof from benzene gave an analytical sample melting at 172.0°–174.5° C.

NMR (CDCl$_3$, δ ppm): 1.54 (9H, s), 6.07 (1H, bs), 7.3–7.6 (4H, m).

Analysis calculated for $C_{11}H_{14}Br_2N_2S$: C 36.08; H 3.85; N 7.65; Found: C 36.29; H 3.63; N 7.64.

EXAMPLE A-10

N-(3,5-dibromophenyl)-N'-t-pentylthiourea

A solution of 5.6 g of 3,5-dibromobenzene and 0.9 g of thiophosgene in 76 ml of benzene was refluxed for 1.5 hours, cooled to room temperature and filtered to remove insoluble matter. To the filtrate was added 3.2 g of t-pentylamine and the mixture stirred at room temperature for 1.5 hours. The reaction mixture was evaporated in vacuo and a small amount of cyclohexane was added to the residue. The resulting crystals were recovered by filtration to give 2.5 g of the title compound. Recrystallization of a portion thereof from cyclohexane gave an analytical sample melting at 147.0°–149.0° C.

NMR (CDCl$_3$, δ ppm): 0.90 (3H, t), 1.49 (6H, s), 1.91 (2H, q), 5.97 (1H, bs), 7.3–7.4 (3H, m), 7.54 (1H, t).

Analysis calculated for $C_{12}H_{16}Br_2N_2S$: C 37.91; H 4.24; N 7.37; Found: C 37.85; H 4.12; N 7.31.

EXAMPLE A-11

N-t-butyl-N'-(3-chloro-5-fluorophenyl)thiourea 3.9 g of 3-chloro-5-fluoroaniline (Zh. Obshch. Khim., 35, 2055(1965)) was dissolved in 70 ml of benzene. To the solution was added 1.0 g of thiophosgene in 10 ml of benzene dropwise. The mixture was refluxed for 3 hours, cooled to room temperature and filtered to remove insoluble matter. The filtrate was evaporated in vacuo and filtered again to remove insoluble matter. To the ice-cooled filtrate dissolved in 30 ml of benzene was added 1.4 g of t-butylamine with stirring. The mixture was stirred for 2 hours at room temperature and evaporated in vacuo. The resulting crystals were filtered off and recrystallized from cyclohexane to give 1.1 g of the title compound melting at 135.0°–137.0° C.

NMR (CDCl$_3$, δ ppm): 1.54 (9H, s), 6.12 (1H, bs), 6.8–7.1 (3H, m), 7.44 (1H, bs).

Analysis calculated for $C_{11}H_{14}ClFN_2S$: C 50.67; H 5.41; N 10.74; Found: C 50.71; H 5.33; N 10.86.

EXAMPLE A-12

N-(3-chloro-5-fluorophenyl)-N'-t-pentylthiourea

A solution of 8.5 g of 3-chloro-5-fluoroaniline in 150 ml of benzene was refluxed. To the solution was added 2.2 g of thiophosgene in 10 ml of benzene dropwise with stirring. The mixture was stirred at the same temperature for 3 hours, cooled to room temperature and filtered to remove insoluble matter. The filtrate was evaporated in vacuo and filtered again to remove insoluble matter. The filtrate was evaporated in vacuo. The residue was purified by silica gel column chromatography using n-hexane as a solvent. The resulting oil was dissolved in 30 ml of benzene and reacted with 3.4 g of t-pentylamine with stirring at room temperature for 30 minutes. The reaction mixture was evaporated in vacuo and the resulting solid recrystallized from cyclohexane to give 2.2 g of the title compound as colorless needles melting at 116.0°–117.5° C. NMR (DMSO-d$_6$, δ ppm): 0.82 (3H, t), 1.42 (6H, s), 1.93 (2H, q), 7.0–7.1 (1H, m), 7.4–7.7 (3H, m), 9.58 (1H, bs).

Analysis calculated for $C_{12}H_{16}ClFN_2S$: C 52.45; H 5.87; N 10.20; Found: C 52.47; H 5.84; N 10.21.

EXAMPLE A-13

N-(3-bromo-5-fluorophenyl)-N'-t-pentylthiourea 10.7 g of 3-bromo-5-fluoroaniline (see, Example A-14) was dissolved in 250 ml of benzene. To the solution was added 2.16 g of thiophosgen in 10 ml of benzene dropwise under reflux. The mixture was stirred at the same temperature for 1.5 hours, cooled to room temperature and filtered to remove insoluble matter. The filtrate was evaporated in vacuo and the resulting solid was dissolved in 50 ml of benzene. To the ice-cooled solution was added 5.6 g of t-pentylamine dropwise and the mixture stirred at room temperature for 1 hour. The reaction mixture was evaporated in vacuo. The resulting solid was purified by silica gel column chromatography using chloroform as a solvent, and then recrystallized from cyclohexane to give 2.2 g of the title compound melting at 123.0°–124.0° C.

NMR (DMSO-d$_6$, δ ppm): 0.82 (3H, t), 1.42 (6H, s), 1.93 (2H, q), 7.1–7.3 (1H, m), 7.4–7.7 (3H, m), 9.56 (1H, bs).

Analysis calculated for $C_{12}H_{16}BrFN_2S$: C 45.15; H 5.05; N 8.78; Found: C 45.18; H 4.99; N 8.80.

EXAMPLE A-14

3-bromo-5-fluoroaniline

Step 1:

A solution of 20.0 g of 4-fluoro-2-nitroaniline and 500 mg of anhydrous ferric chloride in 180 ml of acetic acid was heated to 60°–70° C. with vigorous stirring. To the solution was added dropwise 20.5 g of bromine dissolved in 40 ml of acetic acid at a temperature below 70° C. The mixture was stirred at the same temperature for 2 hours, cooled to room temperature and poured into 300 ml of ice-water. The resulting crystals were filtered off and dissolved in 200 ml of ethyl acetate. The solution was washed with aqueous solution of potassium hydrogen carbonate, dried and evaporated to dryness in vacuo. The residue was purified by silica gel column chromatography using a 20:1 mixture of n-hexane and ethyl acetate to give 18.0 g of 2-bromo-4-fluoro-6-nitroaniline. Recrystallization of a portion thereof from cyclohexane gave an analytical sample melting at 73.0°–75.0° C.

NMR (CDCl$_3$, δ ppm): 6.50 (2H, bs), 7.5–7.7 (1H, m), 7.8–8.0 (1H, m).

Analysis calculated for C$_6$H$_4$BrFN$_2$O$_2$: C 30.66; H 1.72; N 11.92; Found: C 30.64; H 1.73; N 12.01.

Step 2:

A solution of 15.7 g of 2-bromo-4-fluoro-6-nitroaniline in 200 ml of 50% sulfuric acid was cooled to −10° to −5° C. To this was added a solution of 8.1 g of sodium nitrate in 15 ml of water dropwise at a temperature below 0° C. The mixture was stirred at the same temperature for 1.5 hours.

After the addition of 27 ml of ethanol and 6.7 g of ferric sulfate heptahydrate, the mixture was stirred until bubbling was stopped, and then filtered to remove insoluble matter. The insoluble matter and the filtrate were extracted, respectively, with ethyl acetate. Both extracts were combined together and evaporated in vacuo to give 11.4 g of 1-bromo-3-fluoro-5-nitrobenzene.

NMR (CDCl$_3$, δ ppm): 7.5–7.7 (1H, m), 7.8–8.0 (1H, m), 8.1–8.3 (1H, m).

Step 3:

A suspension of 29.0 g of iron powder and 20.0 g of ammonium chloride in 50 ml of water was heated to 90° C. with vigorous stirring. To this was added 24.0 g of 1-bromo-3-fluoro-5-nitrobenzene portionwise. The mixture was refluxed for 4 hours, cooled to room temperature and filtered to remove insoluble matter. The insoluble matter and the filtrate were extracted, respectively, with ethyl acetate. Both extracts were combined together and evaporated in vacuo to give 12.1 g of the title compound. Vacuum distillation of a portion thereof gave an analytical sample boiling at 103.0°–105.0° C. /7 mm Hg.

NMR (DMSO-d$_6$, δ ppm): 5.73 (2H, bs), 6.2–6.4 (1H, m), 6.4–6.7 (2H, m).

Analysis calculated for C$_6$H$_5$BrFN; C 37.92; H 2.65; N 7.37; Found: C 37.83; H 2.68; N 7.36.

Hydrochloride, m.p. 216.0°–219.0° C. (decomp.) from isopropyl alcohol.

NMR (DMSO-d$_6$, δ ppm): 6.7–6.8 (1H, m), 6.9–7.1 (2H, m), 7.98 (3H, bs).

Analysis calculated for C$_6$H$_6$BrClFN: C 31.82; H 2.67; N 6.18; Found: C 31.64; H 2.69; N 6.15.

PART B. PREPARATION OF INVENTIVE COMPOUNDS.

EXAMPLE B-1

N-t-butyl-N'-cyano-N''-(3,5-dichlorophenyl)-guanidine

To a solution of 21.0 g of N-t-butyl-N'-(3,5-dichlorophenyl)thiourea produced in Example A-1 in 200 ml of THF were added 21.4 g of DCC and 0.73 g of triethylamine. The mixture was refluxed for 3 hours and evaporated in vacuo. The residue was extracted with petroleum ether. The extract was evaporated in vacuo to give N-t-butyl-N'-(3,5-dichlorophenyl)carbodiimide as an oil.

To a solution of this oil in 100 ml of THF were added 6.5 g of cyanamide and 1 ml of diisopropylethylamine. The mixture was refluxed for 40 hours and evaporated in vacuo. The residue was recrystallized from isopropyl alcohol to give 14.0 g of the title compound as colorless needles melting at 193.0°–195.0° C.

NMR (DMSO-d$_6$, δ ppm): 1.34 (9H, s), 7.09 (2H, d), 7.23 (1H, t); 7.37 (1H, bs), 9.27 (1H, bs).

Analysis calculated for C$_{12}$H$_{14}$Cl$_2$N$_4$: C 50.54; H 4.95; N 19.65; Found: C 50.53; H 4.89; N 19.68.

EXAMPLE B-2

N-cyano-N'-(3,5-dichlorophenyl)-N''-t-pentylguanidine

To a solution of 3.0 g of N-(3,5-dichlorophenyl)-N'-t-pentylthiourea produced in Example A-2 in 25 ml of THF were added 2.44 g of DCC and 0.36 g of triethylamine. The mixture was refluxed for 3 hours and evaporated in vacuo. The residue was extracted with petroleum ether. The extract was evaporated in vacuo to give N-(3,5-dichlorophenyl)-N'-t-pentylcarbodiimide as an oil. To a solution of this oil in 30 ml of THF were added 1.0 g of cyanamide and 0.1 ml of diisopropylethylamine. The mixture was refluxed for 40 hours and evaporated in vacuo. The residue was recrytallized from diisopropyl ether-ethyl acetate mixture to give 1.9 g of the title compound as colorless needles melting at 151.0°–153.0° C.

NMR (DMSO-d$_6$, δ ppm): 0.82 (3H, t), 1.29 (6H, s), 1.70 (2H, q), 7.08 (2H, d), 7.2–7.3 (2H, m), 9.30 (1H, bs).

Analysis calculated for C$_{13}$H$_{16}$Cl$_2$N$_4$: C 52.18; H 5.39; N 18.73; Found: C 52.26; H 5.41; N 18.79.

EXAMPLE B-3

N-cyano-N'-(3,5-dichlorophenyl)-N''-(1,1-dimethylbutyl)guanidine

To a solution of 3.0 g of N-(3,5-dichlorophenyl)-N'-(1,1-dimethylbutyl)thiourea produced in Example A-3 in 50 ml of dichloromethane were added 5.2 g of triphenylphosphine, 3.1 g of carbon tetrachloride and 2.0 g of triethylamine. The mixture was refluxed for 6 hours, and then evaporated in vacuo. The residue was extracted with petroleum ether. The extract was evaporated in vacuo to give N-(3,5-dichlorophenyl)-N'-(1,1-dimethylbutyl)carbodiimide as an oil. To a solution of this oil in 20 ml of DMF were added 1.6 g of cyanamide and 0.1 ml of diisopropylethylamine. The mixture was stirred at 100° C. for 6 hours, cooled to room temperature and poured into 400 ml of water. The resulting crystals were filtered off, washed with small amount of cyclohexane, and purified by silica gel column chromatography using chloroform as a solvent to give 1.2 g of the title compound. Recrystallization from cyclohexane gave 1.1 g of colorless platelets melting at 115.0°–117.0° C.

NMR (DMSO-d$_6$, δ ppm): 0.88 (3H, t), 1.2–1.4 (2H, m), 1.29 (6H, s), 1.6–1.7 (2H, m), 7.08 (2H, d), 7.23 (1H, t), 7.27 (1H, bs), 9.29 (1H, bs).

Analysis calculated for C$_{14}$H$_{18}$Cl$_2$N$_4$: C 53.68; H 5.79; N 17.89; Found: C 53.67; H 5.78; N 17.91.

EXAMPLE B-4

N-cyano-N'-(3,5-dichlorophenyl)-N''-(1,1,2-trimethylpropyl)guanidine

To a solution of 2.3 g of N-(3,5-dichlorophenyl)-N'-(1,1,2-trimethylpropyl)thiourea produced in Example A-4 in 50 ml of dichloromethane were added 3.9 g of triphenylphosphine, 2.4 g of carbon tetrachloride and 1.5 g of triethylamine. The mixture was refluxed for 3 hours and evaporated in vacuo. The residue was extracted with petroleum ether. The extract was evaporated in vacuo to give N-(3,5-dichlorophenyl)-N'-(1,1,2-trimethylpropyl)carbodiimide as an oil. To a solution of this oil in 20 ml of DMF were added 1.3 g of cyanamide and 0.1 ml of diisopropylethylamine. The mixture was stirred at 120° C. for 12 hours, cooled to room temperature and poured into 600 ml of water. The resulting crystals were collected by filtration and purified by silica gel column chromatography using chloroform as a solvent to yield 1.6 g of crude product. Recrystallization from benzene-cyclohexane mixture gave 1.2 g of the title compound as colorless platelets melting at 167.0°–170.0° C.

NMR (DMSO-d$_6$, δ ppm): 0.84 (6H, d), 1.25 (6H, s), 2.3–2.5 (1H, m), 7.0–7.1 (2H, m), 7.2–7.3 (2H, m), 9.27 (1H, bs).

Analysis calculated for $C_{14}H_{18}Cl_2N_4$: C 53.68; H 5.79; N 17.89; Found: C 53.70; H 5.76; N 17.86.

EXAMPLE B-5

N-cyano-N'-(3,5-dichlorophenyl)-N''-(1-ethyl-1-methylpropyl)guanidine

To a solution of 4.5 g of N-(3,5-dichlorophenyl)-N'-(1-ethyl-1-methylpropyl)thiourea produced in Example A-5 and 5.8 g of triphenylphosphine in 60 ml of dichloromethane were added 2.2 g of triethylamine and 3.4 g of carbon tetrachloride. The mixture was refluxed for 4 hours, cooled to room temperature and evaporated in vacuo. The residue was stirred with n-hexane and the resulting solid matter was removed by filtration. The filtrate was evaporated to give N-(3,5-dichlorophenyl)-N'-(1-ethyl-1-methylpropyl)carbodiimide as an oil. To a solution of this oil in 20 ml of DMF were added 3.4 g of cyanamide and 0.1 ml of diisopropylethylamine. The mixture was stirred at 100° C. for 40 minutes, cooled to room temperature and poured into water. The resulting crystals were filtered off and recrystallized from benzene to give 3.5 g of the title compound as colorless flakes melting at 148.0°–150.0° C.

NMR (DMSO-d$_6$, δ ppm): 0.81 (6H, t), 1.22 (3H, s), 1.5–1.9 (4H, m), 7.08 (2H, d), 7.15 (1H, bs), 7.23 (1H, t), 9.30 (1H, bs).

Analysis calculated for $C_{14}H_{18}Cl_2N_4$: C 53.68; H 5.79; N 17.89; Found: C 53.80; H 5.77; N 17.96.

EXAMPLE B-6

N-cyano-N'-(3,5-dichlorophenyl)-N''-(1,2,2-trimethylpropyl)guanidine

To a solution of 2.5 g of N-(3,5-dichlorophenyl)-N'-(1,2,2-trimethylpropyl)thiourea produced in Example A-6 in 50 ml of THF were added 2.2 g of DCC and 0.36 g of triethylamine. The mixture was refluxed for 4 hours and evaporated in vacuo. The residue was extracted with petroleum ether. The extract was evaporated in vacuo to give N-(3,5-dichlorophenyl)-N'-(1,2,2-trimethylpropyl)carbodiimide as an oil. To a solution of this oil in 20 ml of THF were added 1.0 g of cyanamide and 1 ml of diisopropylethylamine. The mixture was refluxed for 40 hours and evaporated in vacuo. The residue was recrystallized from benzene to give 1.2 g of the title compound as colorless needles melting at 154.0°–156.0° C.

NMR (DMSO-d$_6$, δ ppm): 0.90 (9H, s), 1.07 (3H, d), 3.7–3.9 (1H, m), 7.2–7.4 (4H m), 9.27 (1H, bs).

Analysis calculated for $C_{14}H_{18}Cl_2N_4$: C 53.68; H 5.79; N 17.89; Found: C 53.76; H 5.83; N 17.92.

Example B-7

N-cyano-N'-(3,5-dichlorophenyl)-N''-(1,1-diethylpropyl)guanidine

To a solution of 810 mg of N-(3,5-dichlorophenyl)-N'-(1,1-diethylpropyl)thiourea produced in Example A-7 and 800 mg of triphenylphosphine in 10 ml of dichloromethane were added 380 mg of triethylamine and 590 mg of carbon tetrachloride. The mixture was refluxed for 4 hours and evaporated in vacuo. The residue was stirred with n-hexane and filtered to remove solid matter. The filtrate was evaporated in vacuo and the residue was purified by silica gel column chromatography using n-hexane as a solvent to give 640 mg of N-(3,5-dichlorophenyl)-N'-(1,1-diethylpropyl)carbodiimide as an oil. To a solution of this oil in 5 ml of DMF were added 470 mg of cyanamide and 0.05 ml of diisopropylethylamine. The mixture was stirred at 100° C. for 3 hours, cooled to room temperature and poured into water. The resulting crystals were collected and recrystallized from benzene to give 480 mg of the title compound as colorless needles melting at 178.5°–180.5° C.

NMR (DMSO-d$_6$, δ ppm): 0.77 (9H, t), 1.67 (6H, q), 7.00 (1H, bs), 7.06 (2H, d), 7.23 (1H, t), 9.32 (1H, bs)

Analysis calculated for $C_{15}H_{20}Cl_2N_4$: C 55.05; H 6.16; N 17.12; Found: C 55.06; H 6.15; N 17.15.

Example B-8

N-t-butyl-N'-cyano-N''-(3,5-difluorophenyl)guanidine

To a solution of 1.5 g of N-t-butyl-N'-(3,5-difluorophenyl)thiourea produced in Example A-8 in 27 ml of THF were added 0.46 g of cyanamide, 2.2 g of DCC and 0.14 ml of diisopropylethylamine. The mixture was refluxed for 24 hours and evaporated in vacuo. The residue was mixed with 100 ml of benzene and the resulting crystals were filtered off. The filtrate was concentrated in vacuo. The residue was purified by silica gel column chromatography using a 9:1 mixture of benzene-ethyl acetate as a solvent to give 0.8 g of crude product. Recrystallization from benzene-cyclohexane mixture gave 0.5 g of the title compound as colorless needles melting at 170.0°–172.0° C.

NMR (CDCl$_3$, δ ppm): 1.39 (9H, s), 4.85 (1H, bs), 6.6–6.9 (3H, m), 8.53 (1H, bs).

Analysis calculated for $C_{12}H_{14}F_2N_4$: C 57.13; H 5.59; N 22.21; Found: C 57.19; H 5.58; N 22.24.

EXAMPLE B-9

N-t-butyl-N'-cyano-N''-(3,5-dibromophenyl)guanidine

To a solution of 3.5 g N-t-butyl-N'-(3,5-dibromophenyl)thiourea produced in Example A-9 in 80 ml of dichloromethane were added 5.0 g of triphenylphosphine, 3.0 g of carbon tetrachloride and 1.9 g of triethylamine. The mixture was refluxed for 4 hours and evaporated in vacuo. The residue was extracted with petroleum ether and the extract evaporated in vacuo to give N-t-butyl-N'-(3,5-dibromophenyl)carbodiimide as an oil. To a solution of this oil in 30 ml of DMF were added 1.9 g of cyanamide and 0.1 ml of diisopropylethylamine. The mixture was stirred at 100° C. for 4 hours, cooled to room temperature and poured into 700 ml of water. The resulting crystals were collected, washed with small amount of cyclohexane and recrystallized from benzene to give 2.0 g of the title compound as colorless needles melting at 189.0°–191.0° C.

NMR (DMSO-d$_6$, δ ppm): 1.33 (9H, s), 7.26 (2H, d), 7.38 (1H, bs), 7.46 (1H, t), 9.26 (1H, bs).

Analysis calculated for C$_{12}$H$_{14}$Br$_2$N$_4$: C 38.53; H 3.77; N 14.98; Found: C 38.53; H 3.78; N 15.02.

EXAMPLE B-10

N-cyano-N'-(3,5-dibromophenyl)-N''-t-pentylguanidine

To a solution of 2.4 g of N-(3,5-dibromophenyl)-N'-t-pentylthiourea produced in Example A-10 in 55 ml of dichloromethane were added 3.3 g of triphenylphosphine, 2.0 g of carbon tetrachloride and 1.3 g of triethylamine. The mixture was refluxed for 4 hours and evaporated in vacuo. The residue was extracted with petroleum ether and the extract evaporated in vacuo to give N-(3,5-dibromophenyl)-N'-t-pentylcarbodiimide as an oil. To a solution of this oil in 20 ml of DMF were added 1.2 g of cyanamide and 0.1 ml of diisopropylethylamine. The mixture was stirred at 100° C. for 3 hours, cooled to room temperature and poured into 600 ml of water. The resulting crystals were collected, washed with a small amount of cyclohexane and recrystallized from ethanol to give 0.9 g of the title compound as colorless needles melting at 168.0°–170.0° C.

NMR (DMSO-d$_6$, δ ppm): 0.82 (3H, t), 1.28 (6H, s), 1.69 (2H, q), 7.2–7.4 (3H, m), 7.46 (1H, t), 9.28 (1H, bs).

Analysis calculated for C$_{13}$H$_{16}$Br$_2$N$_4$: C 40.23; H 4.16; N 14.44; Found: C 40.23; H 4.15; N 14.43.

Example B-11

N-t-butyl-N'-(3-chloro-5-fluorophenyl)-N''-cyanoguanidine

To a solution of 1.04 g of N-t-butyl-N'-(3-chloro-5-fluorophenyl)thiourea produced in Example A-11 in 25 of dichloromethane were added 4.18 g of triphenylphosphine, 2.53 g of carbon tetrachloride and 1.61 g of triethylamine. The mixture was refluxed for 2 hours and evaporated in vacuo. The residue was chromatographed on a silica gel column using cyclohexane as a solvent to give N-t-butyl-N'-(3-chloro-5-fluorophenyl)-carbodiimide as an oil. To a solution of this oil in 1.5 ml of DMF were added 500 mg of cyanamide and 0.1 ml of diisopropylethylamine. The mixture was stirred at 100° C. overnight, cooled to room temperature, poured into ice-water, and extracted with ethyl acetate. The extract was evaporated in vacuo to dryness and the residue recrystallized from isopropyl alcohol to give 0.1 g of the title compound as colorless needles melting at 156.0°–157.0° C.

NMR (DMSO-d$_6$, δ ppm): 1.34 (9H, s), 6.8–7.2 (3H, m), 7.38 (1H, bs), 9.31 (1H, bs).

Analysis calculated for C$_{12}$H$_{14}$ClFN$_4$: C 53.63; H 5.25; N 20.85; Found: C 53.72; H 5.26; N 20.87.

Example 12

N-(3-chloro-5-fluorophenyl)-N'-cyano-N''-t-pentylguanidine

To a solution of 3.5 g of N-(3-chloro-5-fluorophenyl)-N'-t-pentylthiourea produced in Example A-12 in 20 ml of dichloromethane were added 7.4 g of triphenylphosphine, 4.9 g of carbon tetrachloride and 2.85 g of triethylamine. The mixture was refluxed for 2 hours and evaporated in vacuo. The residue was extracted with petroleum ether and the extract was evaporated in vacuo to give N-(3-chloro-5-fluorophenyl)-N'-t-pentylcarbodiimide as an oil. To a solution of this oil in 20 ml of DMF were added 1.31 g of cyanamide and 2 ml of diisopropylethylamine. The mixture was stirred at 100° C. for 15 hours, cooled to room temperature, poured into ice-water and extracted with ethyl acetate. The extract was evaporated in vacuo. The residue was chromatographed on a silica gel column using chloroform as a solvent and recrystallized from isopropyl alcohol to give 1.0 g of the title compound as colorless needles melting at 130°–131.0° C.

NMR (DMSO-d$_6$, δ ppm): 0.82 (3H, t), 1.29 (6H, s), 1.70 (2H, q), 6.8–7.1 (3H, m), 7.25 (1H, bs), 9.31 (1H, bs).

Analysis calculated for C$_{13}$H$_{16}$ClFN$_4$: C 55.22; H 5.70; N 19.82; Found: C 55.39; H 5.68; N 19.90.

EXAMPLE B-13

N-(3-bromo-5-fluorophenyl)-N'-cyano-N''-t-pentylguanidine

To a solution of 2.0 g of N-(3-bromo-5-fluorophenyl)-N'-t-pentylthiourea produced in Example A-13 in 20 ml of dichloromethane were added 3.1 g of triphenylphosphine, 2.3 g of carbon tetrachloride and 0.6 g of triethylamine. The mixture was refluxed for 2 hours and evaporated in vacuo. The residue was extracted with petroleum ether. The extract was evaporated in vacuo to remove the solvent whereupon N-(3-bromo-5-fluorophenyl)-N'-t-pentylcarbodiimide was obtained as an oil. This oil was further purified by silica gel column chromatography using cyclohexane as a solvent. To a solution of this oil in 20 ml of DMF were added 0.27 g of cyanamide and 1 ml of diisopropylethylamine. The mixture was stirred at 100° C. for 15 hours, cooled to room temperature, poured into ice-water and extracted with ethyl acetate. After evaporating the solvent in vacuo, the extract was purified by silica gel column chromatography using chloroform as a solvent and recrystallized from benzene-n-hexane mixture to give 0.7 g of the title compound as colorless needles melting at 129.0°–130.0° C.

NMR (DMSOd$_6$, δ ppm): 0.82 (3H, t), 1.28 (6H, s), 1.70 (2H, q), 6.8–7.3 (4H, m), 9.30 (1H, bs).

Analysis calcuataed for C$_{13}$H$_{16}$BrFN$_4$: C 47.72; H 4.93; N 17.12; Found: C 47.75; H 4.90; N 17.03.

PART C. PHARMACOLOGY

1. SMOOTH MUSCLE RELAXATION

Male guinia pigs weighing 300–600 g were stunned by blow on the head. Taeniae were isolated from the caecum and cut into length of about 1 cm to prepare a plurality of test specimens. These specimens were suspended in an organ bath filled with MOPS-PSS containing 129.7 mM of NaCl, 5.9 mM of KCl, 2.54 mM of CaCl$_2$, 1.19 mM of MgCl$_2$, 10.0 mM of 3-(N-morpholino)propanesulfonic acid (MOPS) and 11.1 mM of glucose, pH 7.4. The bathing solution was continuously bubbled with 100% O$_2$ gas and maintained at 37°±1° C. Resting tension of each specimen was adjusted to 1 g and the spontaneous response was recorded isotonically. The specimens were allowed to stabilize before starting the test. Test compound was cumulatively added to the bathing solution. A relaxation induced with papaverine ($10^{-4}$ M) was taken as 100% relaxation. The relaxation effect of each test compound was evaluated in terms of a dose achieving 50% relaxation (ED$_{50}$) determined by the linear regression analysis.

The compounds of this invention obtained in Examples B-1 to B-13 exhibited more potent activities in this test compared to pinacidil, N-cyano-N'-t-pentyl-N''-phenylguanidine (Compound A, J. Med. Chem., 21, 773(1978), N-t-butyl-N'-cyano-N''-(2,6-dichlorophenyl)guanidine (Compound B, ibid.) and 2-nitro-1-anilino-1-(1,2,2-trimethylpropyl)aminoethene (Compound C, U.S. Pat. No. 4,567,188) as shown Table 1 below.

TABLE 1

| Test compound | ED$_{50}$ μM |
|---|---|
| Ex. B-1 (n = 5) | 0.087 |
| Ex. B-2 (n = 5) | 0.026 |
| Ex. B-3 (n = 5) | 0.035 |
| Ex. B-4 (n = 5) | 0.058 |
| Ex. B-5 (n = 5) | 0.081 |
| Ex. B-6 (n = 3) | 0.18 |
| Ex. B-7 (n = 5) | 0.18 |
| Ex. B-8 (n = 5) | 0.18 |
| Ex. B-9 (n = 5) | 0.021 |
| Ex. B-10 (n = 5) | 0.019 |
| Ex. B-11 (n = 5) | 0.066 |
| Ex. B-12 (n = 5) | 0.054 |
| Ex. B-13 (n = 5) | 0.025 |
| Pinacidil (n = 20) | 2.0 |
| Compd. A (n = 5) | 1.8 |
| Compd. B (n = 5) | >100 |
| Compd. C (n = 5) | 2.7 |

2. K+ CHANNEL OPENING ACTIVITY

In order to ascertain that the smooth muscle relaxation activity is proportional to the K+ channel opening activity, the compound of Example B-2 was tested for the K+ channel opening activity in comparison with pinacidil.

$^{86}$Rb+ efflux was selected as the indication of K+ channel opening effect because the K+ channels were considered to be selective also for Rb+. In a similar manner to the test 1, specimens of taenia caecum were suspended in a test tube filled with MOPS-PSS. The bathing solution was continuously bubbled with 100% O$_2$ gas and maintained at 37°±1° C. After an equilibration period for about 45 minutes, the specimens were loaded with $^{86}$Rb+. The efflux from the specimens was measured using a scintillation counter at every 2 minutes interval. The efflux data were expressed in terms of the rate coefficient (the $^{86}$Rb+ efflux just before the test compounds were added were taken as 100%). The effective dose (ED$_{15}$) Producing 15% increase of the rate coefficient by the test compounds were calculated from the linear regression analysis.

As shown in Table 2 below, the results obtained in this test are generally proportional to those obtained in the test 1. This indicates that the smooth muscle relaxation effect of the compounds of this invention is based on their K+ channel opening effect.

TABLE 2

| Test compound | ED$_{15}$, μM (n = 5) |
|---|---|
| Ex. B-2 | 0.27 |
| Pinacidil | 24 |

3. HYPOTENSIVE ACTIVITY

Mongrel dogs of both sexes, weighing 11-22 kg, were anesthetized with sodium pentobarbital (30 mg/kg, i.v.). Mean blood pressure was measured with a carrier amplifier (Nihon Koden, AP-621G) via a pressure transducer (Nihon Koden, TP-200T) connected to the cannulated left femoral artery. Each test compound was dissolved in 0.9% saline containing 50% (v/v) ethanol and injected into the femoral vein in volumes of 0.1 ml/kg. The hypotensive effects of test compounds were evaluated in terms of the maximum decrease in the mean blood pressure (Δ mmHg) at a dose of 30 μg/kg.

The results obtained are shown in Table 3 below.

TABLE 3

| Test compound | Δ mm Hg ± S.E. at 30 μg/kg, i.v. |
|---|---|
| Ex. B-2 (n = 5) | −19.1 ± 4.1 |
| Ex. B-3 (n = 3) | −22.9 ± 3.2 |
| Ex. B-5 (n = 3) | −26.1 ± 1.8 |
| Ex. B-11 (n = 3) | −19.2 ± 4.4 |
| Ex. B-13 (n = 3) | −33.4 ± 0.9 |
| Pinacidil (n = 30) | −11.3 ± 1.1 |

4. ACUTE TOXICITY

Male rats weighing 70-210 g (3-5 rats/group) were fasted overnight and administered orally with the test compound suspended in 5% gum arabic solution. LD$_{50}$ was calculated from the number of death for 7 days using the Weil's method.

The results are shown in Table 4 below.

TABLE 4

| Test compound | LD$_{50}$, mg/kg, p.o. |
|---|---|
| Ex. B-1 | >2000 |
| Ex. B-2 | >2000 |
| Ex. B-5 | >2000 |
| Ex. B-13 | >2000 |
| Pinacidil | 471.9 |

What is claimed is:

1. A compound of the formula:

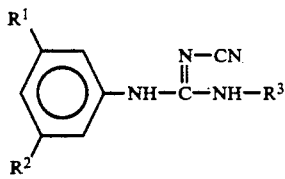

wherein $R^1$ and $R^2$ are independently fluorine, chlorine or bromine atom, and $R^3$ is a C$_4$-C$_7$ alkyl having at least a branch at the C$_1$ position.

2. The compound of claim 1 which is N-cyano-N'-(3,5-dichlorophenyl)-N''-t-pentylguanidine.

3. The compound of claim 1 which is N-cyano-N'-(3,5-dichlorophenyl)-N''-(1,1-dimethylbutyl)guanidine.

4. The compound of claim 1 which is N-cyano-N'-(3,5-dichlorophenyl)-N''-(1-ethyl-1-methylpropyl)-guanidine.

5. The compound of claim 1 which is N-(3-bromo-5-fluorophenyl)-N'-cyano-N''-t-pentylguanidine.

6. A compound of claim 1 which is N-t-butyl-N'-cyano-N''-(3,5-dichlorophenyl)guanidine.

7. A compound of claim 1 which is N-cyano-N'-(3,5-dichlorophenyl)-N''-(1,1,2-trimethylpropyl)guanidine.

8. A compound of claim 1 which is N-cyano-N'-(3,5-dichlorophenyl)-N''-(1,2,2-trimethylpropyl)guanidine.

9. A compound of claim 1 which is N-cyano-N'-(3,5-dichlorophenyl)-N''-(1,1-diethylpropyl)guanidine.

10. A compound of claim 1 which is N-t-butyl-N'-cyano-N''-(3,5-difluorophenyl)guanidine.

11. A compound of claim 1 which is N-t-butyl-N'-cyano-N''-(3,5-dibromophenyl)guanidine.

12. A compound of claim 1 which is N-t-butyl-N'-(3,5-dibromophenyl)-N''-t-pentylguanidine.

13. A compound of claim 1 which is N-t-butyl-N'-(3-chloro-5-fluorophenyl)-N''-cyanoguanidine.

14. A compound of claim 1 which is N-(3-chloro-5-fluorophenyl)-N'-cyano-N''-t-pentylguanidine.

15. A pharmaceutical composition for the treatment of circulation system disorders comprising an effective amount of a compound of claim 1 in admixture with a pharmaceutically acceptable carrier therefor.

* * * * *